(12) United States Patent
Chole (10) Patent No.: US 7,540,287 B2
(45) Date of Patent: Jun. 2, 2009

(54) PATIENT IDENTIFICATION SYSTEM AND METHOD FOR PREVENTING WRONG SITE PROCEDURE

(75) Inventor: Richard Arthur Chole, St. Louis, MO (US)

(73) Assignee: Washington University, St. Louis, MO (US)

( * ) Notice: Subject to any disclaimer, the term of this patent is extended or adjusted under 35 U.S.C. 154(b) by 965 days.

(21) Appl. No.: 10/910,597

(22) Filed: Aug. 3, 2004

(65) Prior Publication Data
US 2006/0027240 A1  Feb. 9, 2006

(51) Int. Cl.
*A61B 19/00* (2006.01)
(52) U.S. Cl. ...................................... 128/899
(58) Field of Classification Search ......... 128/297–899, 128/920–923; 600/300
See application file for complete search history.

(56) References Cited

U.S. PATENT DOCUMENTS

| | | | |
|---|---|---|---|
| 4,682,155 A | 7/1987 | Shirley | |
| 4,857,713 A | 8/1989 | Brown et al. | |
| 5,079,541 A | 1/1992 | Moody | |
| 5,107,862 A | 4/1992 | Fabian et al. | |
| 5,188,126 A | 2/1993 | Fabian et al. | |
| 5,190,059 A | 3/1993 | Fabian et al. | |
| 5,272,318 A | 12/1993 | Gorman et al. | |
| 5,329,944 A | 7/1994 | Fabian et al. | |
| 5,381,487 A | 1/1995 | Shamos et al. | |
| 5,493,805 A | 2/1996 | Penuela et al. | |
| 5,512,879 A | 4/1996 | Stokes | |
| 5,793,290 A | 8/1998 | Eagleson et al. | |
| 5,883,576 A | 3/1999 | De La Huerga | |
| 6,026,818 A | 2/2000 | Blair et al. | |
| 6,104,295 A | 8/2000 | Gaisser et al. | |
| 6,195,009 B1 | 2/2001 | Iriazrry et al. | |
| 6,346,886 B1 | 2/2002 | De La Huerga | |
| D464,280 S | 10/2002 | Kim et al. | |
| 6,464,689 B1 * | 10/2002 | Qin et al. ...................... 606/1 |
| 6,700,489 B1 | 3/2004 | Easter et al. | |
| 2001/0004239 A1 | 6/2001 | Irizarry et al. | |
| 2002/0063627 A1 | 5/2002 | Makiyama et al. | |
| 2002/0084904 A1 | 7/2002 | De La Huerga | |

(Continued)

FOREIGN PATENT DOCUMENTS

DE     19804028 A1    8/1998

OTHER PUBLICATIONS

Wasek, S., "What Kind of Patient-Tracking is for You?," Outpatient Surgery Magazine, www.outpatientsurgery.com, Jul. 2004, pp. 1-6.

(Continued)

*Primary Examiner*—Samuel G Gilbert
(74) *Attorney, Agent, or Firm*—Senniger Powers LLP (57) ABSTRACT

A patient equipped with a device in a first mode is scheduled for a procedure in a procedure room at a facility with pre-procedure rules (e.g., requiring procedure site marking). Only a surgeon or other authorized individual is permitted to change the first mode to a second mode after complying with the rules (e.g., marking a site on the patient's body). A detector is located at or near the entrance of the procedure room for detecting devices having the first mode. If the first mode is detected, an alarm is provided indicating that the rule may not have been followed.

43 Claims, 3 Drawing Sheets

U.S. PATENT DOCUMENTS

2002/0179094 A1*  12/2002  Perlow .................. 128/897
2003/0140928 A1*   7/2003  Bui et al. .............. 128/898
2003/0182815 A1   10/2003  Carlson, II
2005/0109350 A1*   5/2005  Luloh .................... 128/898

OTHER PUBLICATIONS

Unknown, "Leading Medical, Health Care Groups Endorse Joint Commission's New Universal Protocol™ To Prevent Wrong Site Surgery", The Joint Commission on Accreditation of Healthcare Organizations available at http://www.jcaho.org/news+room/press+kits/wss_news_release_1202.htm, Dec. 2003, 3 pages, The Joint Commission on Accreditation of Healthcare Organizations, USA.

Beyea, "Ensuring Correct Site Surgery," AORN Journal, Nov. 2002, vol. 76, No. 5, pp. 880-882, USA.

"Making Health Care Safer: A Critical Analysis of Patient Safety Practices," Evidence Report/Technology Assessment: No. 43, AHRQ Publication No. 01-E058, Jul. 2001, 5 pages, Agency for Healthcare Research and Quality, Rockville, MD, USA.

Cowell, "Wrong-Site Surgery," The Journal of Bone and Joint Surgery, vol. 80-A, No. 4, 463 Editorial, Apr. 1998, USA.

* cited by examiner

PATIENT IDENTIFICATION SYSTEM AND METHOD FOR PREVENTING WRONG SITE PROCEDURE

FIELD OF THE INVENTION

The invention relates generally to a patient identification system which identifies the status of a patient. In particular, the invention relates to a patient identification system and method for monitoring compliance of pre-procedure rules with respect to a particular patient. More particularly, the invention relates to a patient identification system and method for monitoring that a procedure site has been marked on a patient prior to a procedure thereby minimizing the risk of wrong site procedure on the patient.

BACKGROUND OF THE INVENTION

Wrong site procedures performed in hospitals, ambulatory surgery centers and doctor's offices have been identified as a significant category of medical errors jeopardizing the safety of patients. The Joint Commission on Accreditation of Hospital Organizations (JACHO) requires surgeons to physically mark a procedure site on a patient with a marker or other device prior to any invasive procedure. In spite of this standard, surgeons occasionally fail to mark the procedure site or request that someone else, such as a nurse, mark the site. This could result in no site marking or a mismarked site. Without the surgeon marking a procedure site in advance, there is an increased risk that a surgeon may perform a procedure on a wrong site.

Other methods and systems have been proposed to mark a site other than the procedure site. For example, if the surgeon is to operate on a patient's right knee, an indicia or a mark would be placed on the patient's left knee and would show that the left knee is not to be operated on. However, these methods and systems fall short of requiring that the surgeon and not others must mark the procedure site before the procedure.

Thus, there is a need for a system and method which encourages surgeons to mark procedure sites and, thus, assists in preventing wrong site procedures and surgery. There is also a need for a system and method which encourages compliance with pre-procedure rules and, thus, assists in monitoring whether pre-procedure rules have been followed before performing a procedure.

SUMMARY OF THE INVENTION

In one embodiment, the invention is a method for use with a patient scheduled to have a procedure at a particular site on the patient's body. The method assists in preventing the procedure being performed at a site on the patient's body other than the particular site. An enabled device is applied to the patient. The particular site on the patient's body is marked after applying the enabled device to the patient's body. The device applied to the patient is disabled after marking the particular site. The method includes sensing for an enabled device associated with the patient prior to performing the procedure on the patient's body. An alarm is provided when an enabled device is detected prior to performing the procedure on the patient.

In another embodiment, the invention is a method for use with a patient scheduled to have a procedure at a particular site on the patient's body. The method monitors the patient's status to determine whether the particular site has been marked before the procedure is performed. A device in a first mode is applied to or near the patient's body. The particular site on the patient's body is marked after applying the device to the patient's body. The mode of the device is changed from the first mode to a second mode after marking the particular site on the patient's body. An alarm is provided when a device in the first mode is detected prior to the procedure.

In yet another embodiment, the invention is a method for use with one or more patients whereby each particular patient is scheduled to have a particular procedure at a particular site on the body of the particular patient. The method assists in preventing the particular procedure being performed at a site on each patient's body other than the particular site. A device in a first mode is associated with each patient. The mode of the device associated with a particular patient is changed from the first mode to a second mode after marking the particular site of the particular patient. An alarm is provided when one of the devices in the first mode is detected prior to or immediately before performing a procedure.

In accordance with another embodiment, the invention is a system for use with a patient scheduled to have a particular procedure at a particular site on the patient's body where the procedure is to be performed in a procedure room. The system monitors the patient's status to determine whether the particular site has been marked before the procedure is performed. A device has a first mode and is adapted to be applied to or near the patient's body prior to the procedure. A modifying device modifies the first mode to a second mode of the device, the second mode being different from the first mode. The modifying device is adapted for use after the particular site has been marked on the patient's body. A detector located near or in the procedure room detects devices having the first mode. An alarm responsive to the detector provides an indication that a device having the first mode and not having the second mode has been detected.

In a further embodiment, the invention is a system for use with one or more patients whereby each particular patient is scheduled to have a particular procedure at a particular site on the body of the particular patient where the procedures are to be performed in one or more procedure rooms. The system assists in preventing the particular procedure of each patient being performed at a site on each patient's body other than the particular site. One or more devices with each device have a first mode and a second mode. Each device in the first mode is adapted to be applied to or near the body of one of the patients prior to the particular procedure for each patient. A modifying device changes each of the devices from the first mode to the second mode. The modifying device is adapted for use after the particular site has been marked on each patient's body. Each of one or more detectors located near or in one of the procedure rooms detects the first mode of each of the devices. Each of one or more alarms is associated with one of the detectors for providing an indication when its associated detector detects one of the devices having the first mode.

In accordance with yet another embodiment, the invention is a method for use with a patient scheduled to have a procedure at a facility with pre-procedure rules. The method monitors the patient's status to determine whether the patient has been handled in compliance with the pre-procedure rules prior to performing the procedure on the patient. A device in a first mode is associated with the patient. The mode of the device is changed from the first mode to a second mode after complying with the pre-procedure rules. An alarm is provided when a device in the first mode is detected prior to performing the procedure on the patient.

In accordance with a further embodiment, the invention is a system for use with a patient scheduled to have a procedure at a facility with pre-procedure rules. The system monitors the patient's status to determine whether the patient has been handled in compliance with the pre-procedure rules prior to performing the procedure on the patient. A device in a mode is adapted to be associated with the patient prior to the procedure. A modifying device modifies the mode to another mode of the device. The modifying device is adapted for use after complying with the pre-procedure rules. A detector detects the mode of the device. An alarm that is responsive to the detector for providing an indication that a device has a mode which indicates that the pre-procedure rules have not been complied with.

Alternatively, the invention may comprise various other methods and apparatuses.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE INVENTION

Figure 1:
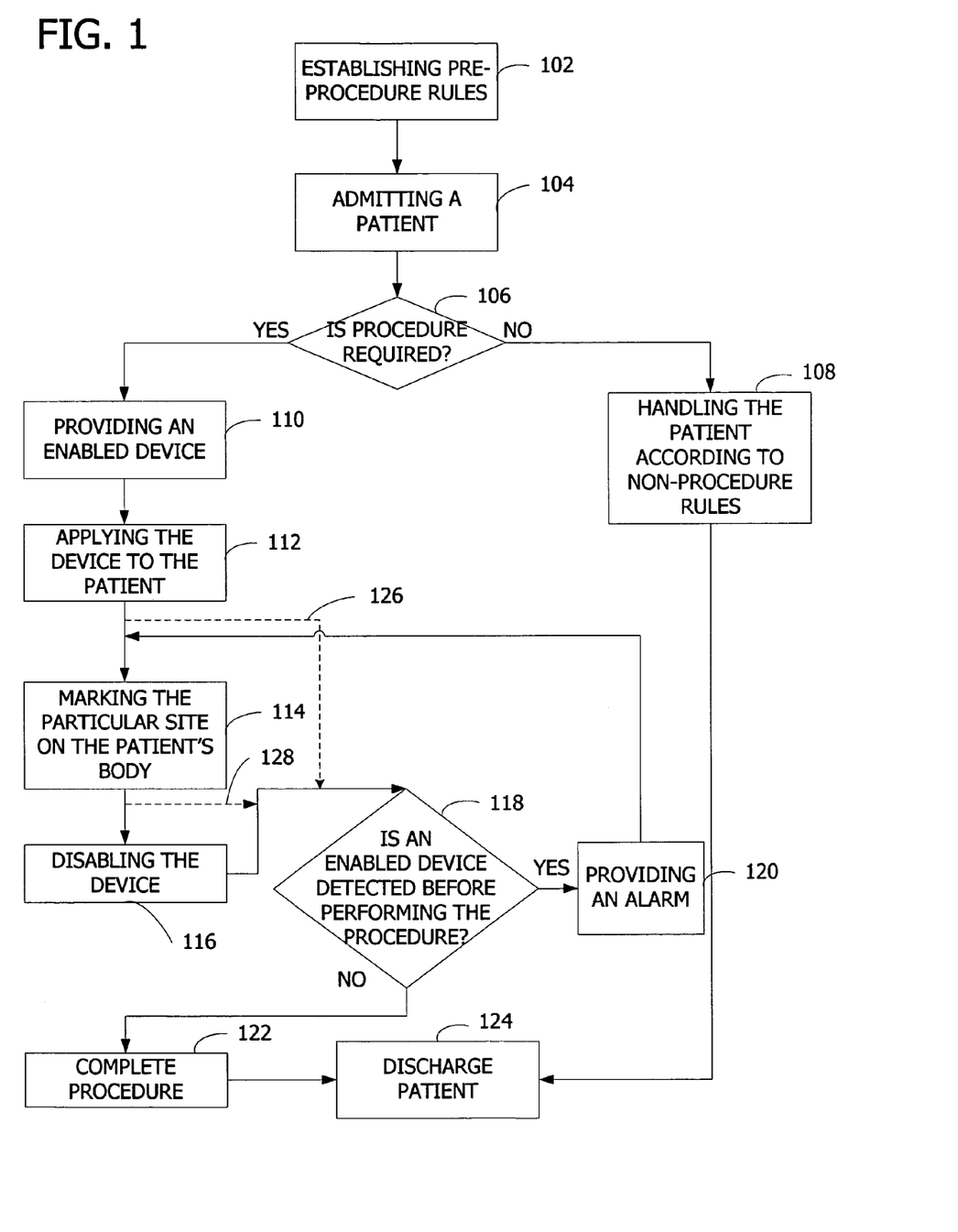
FIG. 1 is a flow chart of an embodiment of a method according to the invention for assisting in preventing wrong site procedures, such as surgeries.
Figure 2:
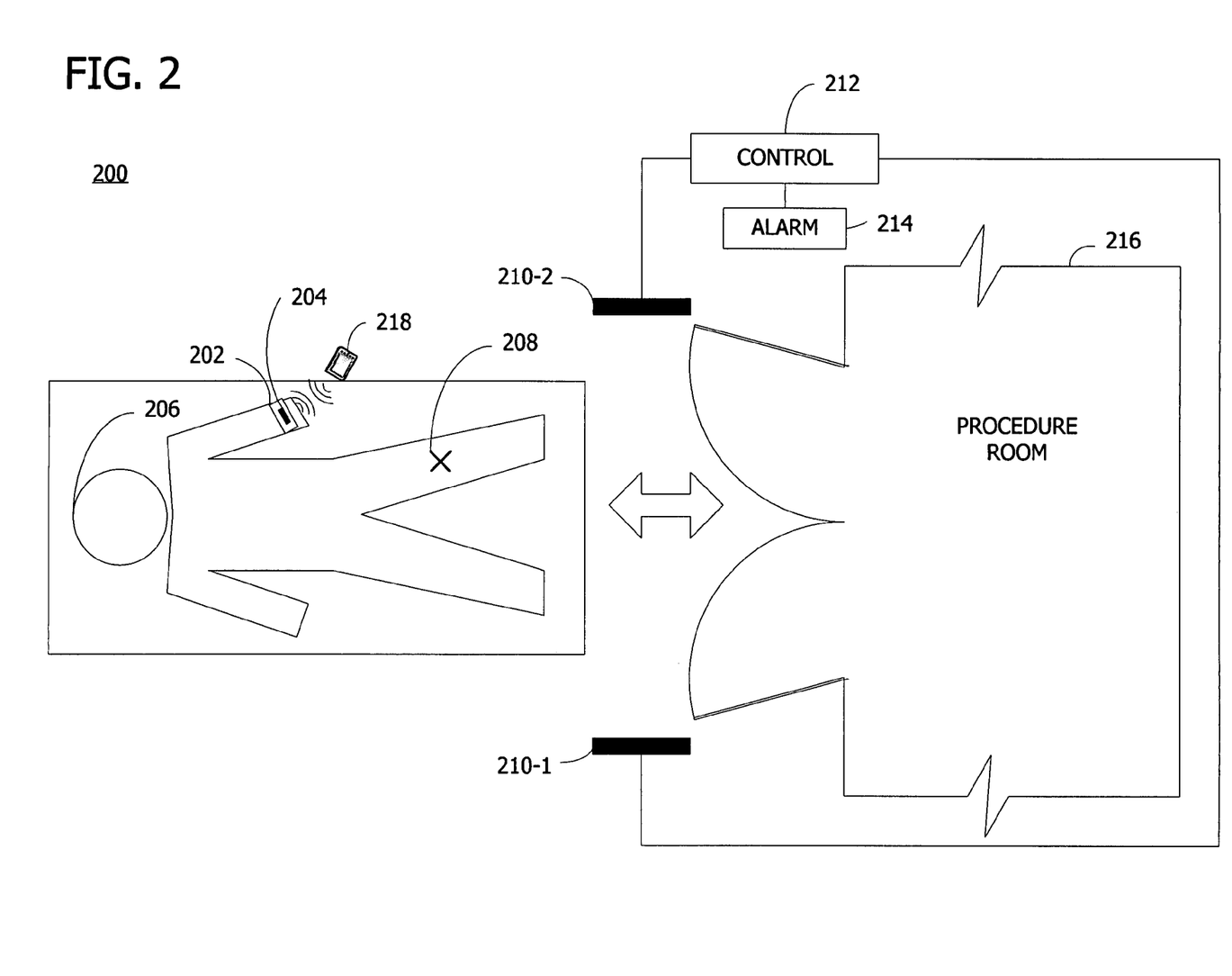
FIG. 2 is a block diagram of an embodiment of a system according to the invention for monitoring that a pre-procedure practice has been followed prior to performing the procedure.

Referring now to the drawings, FIG. 1 is a flow chart illustrating an embodiment of a method according to the invention for assisting in preventing wrong site procedures, such as surgeries, and FIG. 2 is a block diagram illustrating an embodiment of a system according to the invention for monitoring that a procedure is being performed at a particular site.

Facilities, such as hospitals, clinics or specialized medical facilities, frequently establish a set of rules relating to proper handling of patients, such as a patient 206. For example, such a set of rules may include a set of pre-procedure rules, rules for admitting patients, rules for discharging patients, and/or a set of non-procedure rules. By way of example and not limitation, a procedure covered by these rules may be any invasive procedure, such as a surgery or an operation on an anatomic site of a patient's body.

In one embodiment, the facility establishes a set of pre-procedure rules at 102 to ensure proper practices in handling of patients before scheduled procedures. The management of the facility may establish a set of pre-procedure rules to meet its safety or other needs in handling patients prior to scheduled procedures. Alternatively, an outside organization other than the facility, e.g., the American Academy of Orthopaedic Surgeons or other professional or governmental organizations, may recommend a set of pre-procedure practices as a standard to the facilities in handling patients prior to scheduled procedures.

For example, one of the pre-procedure rules may require that patients scheduled for a procedure wear a bracelet indicating the patient's status and that only an authorized individual may modify the bracelet to change a status of the patient 206 scheduled for a procedure. Such patient status would indicate whether the patient is ready for a procedure. In the case of a procedure to be performed at a particular site, the patient's status may relate to whether an authorized individual has or has not pre-marked a procedure site 208 on the body of the patient 206. If the status indicates that the procedure site 208 has not being marked, the patient 206 is not ready for the performance of the procedure and the authorized individual must mark the procedure site 208 prior to or immediately before the performance of the procedure.

In general, the rules may encourage authorized individuals to follow specified pre-procedure practices, such as site marking. In addition, the rules may minimize, inhibit and/or prevent marking of the procedure site 208 on the body of the patient 206 by an unauthorized individual. Also, the rules may assist and/or encourage proper marking or other pre-procedure practices thereby inhibiting or preventing the authorized individual from marking a wrong procedure site on the body of the patient 206 and/or from changing the status of the patient 206 without marking the procedure site 208. In one respect, the rules may protect the patient or otherwise foster a high quality of care for the patient.

Still referring to FIGS. 1 and 2, the process of handling a patient according to the invention begins at 104 when the facility admits patient 206. A nurse, a doctor, or other medical personnel at the facility may perform a preliminary examination or diagnosis after admitting the patient 206. For example, this may include, but is not limited to, measuring vital signs, doctor/patient interviews, x-ray examinations, etc. After this, a determination is made at 106 as to whether a procedure is required or scheduled for the patient 206. It is also contemplated that the determination may be time-consuming and may or may not occur before or after the admission or diagnosis of the patient. If a procedure is not required or scheduled for the patient 206, the patient 206 is handled according to a set of non-procedure rules established by the facility at 108 and will be discharged at 124 according the facility's rules for discharging such patient or other appropriate measures.

After it is determined at 106 that a procedure is required, a time to perform the procedure is scheduled. The scheduled procedure may or may not occur immediately after the determination that the procedure is required. At 110, a device 202 indicating the patient's status is provided to the patient before the scheduled procedure. If the patient had left the facility after the determination at 106, the device 202 may be provided to the patient 206 upon returning to the facility and/or at any time before the scheduled procedure. In another embodiment where the patient 206 does not leave the facility, the device 202 may be provided to the patient 206 after the determination that the procedure is required.

In one embodiment, the device 202 may be a wristband or bracelet embedded with a radio frequency tag 204. In another embodiment where a wristband or bracelet 202 was previously provided to the patient 206 after his/her admission to the facility, the device 202 may be an RF tag 204 affixed to the previously provided wristband or bracelet 202. In yet another embodiment, the device 202 may include a radio frequency identification (RFID) device, an acousto-magnetic device, an electromagnetic device or any other electronic article surveillance device having more than one mode or state, each mode or state being distinctive from the other such as states that are mutually exclusive of one another. For example, in one form the device may have an enabled and a disabled state, so that the device can either be in the enabled state or the disabled state, but not both states and not neither state. By way of example and not limitation, an enabled device 202 may be an active RF wristband. Thus, an "enabled device" may be a device that is not in the same mode or state as that of a "disabled device" where the device has at least these two states or modes. In another embodiment, the "enabled" device may be a device in a first mode, which is different from a second mode, where the device has both the first mode and the second mode. An example of an RF tag includes products manufactured by Checkpoint® Systems, Inc., and an example of an acousto-magnetic tag is includes EAS products manufactured by Sensormatic® Electronics Corporation under the Tyco Fire & Security, a major business segment of Tyco International.

Again, by way of example and not limitation, the device may be an RF wristband which is capable of transmitting a signal independent of or in response to an interrogation signal from an RF deactivator, reader or detector. By way of example and not limitation, the device 204 will hereinafter be referred to as an active (or deactivated) RF wristband 204.

It is contemplated that the device can be any indicator having at least two distinctive modes from the device 204. In the case of marking prior to a procedure, one of the modes would indicate that the particular site has not been marked and the other mode would indicate that the site has been marked. It is also contemplated that a mode may include one or more emitting signals from the RF wristband. For example, a first mode indicating that the particular site has not been marked may correspond to one emitting signal in one frequency range while a second mode indicating the particular site has been marked may correspond to two or more than one emitting signals, each having different frequency ranges or visa versa.

At 112, the active RF wristband 204 is applied to or near the patient 206. In one embodiment, the active RF wristband 204 may be fitted to the wrist or ankle of the patient 206. Alternatively, the active RF wristband 204 may be applied to anything associated with the patient 206 which travels with the patient 206 such as the chart or gurney of the patient 206. When the wristband 204 is first applied to or near the patient 206, it is in a mode (herein the enabled or active mode) which indicates that one or more pre-procedure practice, such as site marking, has not been performed on the patient.

Before changing the mode of the active RF wristband 204, an authorized individual uses a marking instrument or other device to mark the procedure site 208 on the body of the patient 206. In one embodiment where the patient 206 may be subjected to multiple procedures, the authorized individual may mark all procedure sites on the patient's body before changing the mode of the active RF wristband 204. According to the pre-procedure rules, only an authorized individual, such as a surgeon, may change the mode of the active RF wristband 204 and this change is only permitted after the procedure site 208 on the patient's body is marked.

After marking the procedure site 208 on the patient's body at 114, the authorized individual at 116 inactivates or disables the active or enabled RF wristband 204 so that the wristband 204 is now a deactivated RF wristband 204 (e.g., indicating that the status of the patient is such that the pre-procedure practice has been completed with the patient and the patient is ready for the procedure). For example, by disabling the active RF wristband 204 after marking the procedure site 208, the authorized individual confirms that the procedure site 208 has been marked and the patient 206 is ready for the procedure. In other words, the authorized individual has complied with the pre-procedure rules set forth by the facility.

In one embodiment, the authorized individual may use a modifying device 218, such as an RF deactivator, to deactivate, disable, or change the mode of the RF tag of the active RF wristband 204. By way of example and not limitation, the modifying device 218 disables the active RF wristband 204 by transmitting signals containing high electrical charge such that the signals from the deactivator inhibits the circuitry of the RF transponder inside the active RF wristband 204. In another embodiment, the modifying device 218 may be an RF deactivator in the form of a handheld device, a stationary device or a RF shield tag or label for modifying the modes of the identifying device 204. For example, such RF deactivator includes products manufactured by Checkpoint® Systems, Inc., and an example of an acousto-magnetic tag deactivator includes the EAS products manufactured by Sensormatic® Electronics Corporation under the Tyco Fire & Security, a major business segment of Tyco International. In another embodiment, the authorized individual may modify the mode of the active RF wristband 204 by operably affixing additional RF or acousto-magnetic devices such that the additional RF or acousto-magnetic device is in a distinct mode from the mode of the active RF wristband 204. In yet another embodiment, the authorized individual "disables" the active RF wristband 204 by using the modifying device 218 to modify or change the mode of the active RF wristband 204 from a first mode to a second mode. In yet another embodiment, disabling may involve removing the device from the patient.

In yet another embodiment, a surgeon may have a unique code to access the modifying device. For example, a surgeon is required to enter the unique code into a keypad of the modifying device in order to energize the modifying device before changing the mode of the active RF wristband 204. However, unique codes for the surgeons are optional and unnecessary. The system and method of the invention remind the authorized individual to mark the site and to crosscheck to ensure that the procedure site is marked. It is unlikely that a dishonest surgeon will try to defeat the system and method. The system and method are primarily directed to mistakes made because surgeons are in a rush who inadvertently forget to perform all of the required steps in advance.

In yet another embodiment, the modifying device 218 may also provide the marking instrument or devices for the authorized individual to mark the procedure site 208 on the body of the patient 206. For example, the modifying device 218 may contain a pouch or compartment affixed to its housing to hold a marking instrument or device mechanically connected to the modifying device 218, such as by a spiral wire, elastic band, etc. It is also contemplated that in one embodiment, the modifying device 218 may provide an audio or visual notification when the active RF wristband 204 has changed from one mode to another (e.g., has been disabled).

After the authorized individual marks the particular site 218 disables the active RF wristband 204, the patient is taken to a procedure room 110 or other location where the procedure will be performed. At 118, one or more detectors 210-1 and 210-2 positioned at or near the location sense whether a mode of an active RF wristband 204 associated with the patient is present, thus indicating whether the marking of the procedure site 208 has been completed. For example, a RF detector includes products manufactured by Checkpoint® Systems, Inc., and an example of an acousto-magnetic detector includes the EAS products manufactured by Sensormatic® Electronics Corporation under the Tyco Fire & Security, a major business segment of Tyco International. In other words, the detectors 210 monitor the status of patients to confirm that patients entering the procedure room 216 or other location have a disabled device or a device in a second mode indicating that they have been properly prepared according to the pre-procedure rules. The detectors 210 are connected to a control 212 via a wireless or wired connection. Similarly, the control 212 is connected to an alarm 214 via a wireless or wired connection.

For example, the detectors 210 broadcast an interrogating signal to or near the entrance or the interior of the procedure room 216. As discussed earlier, if a hospital is the facility, there may be one pair of detectors 210 for each procedure room 216. In one embodiment, the detectors 210 may be placed at the entrance of the procedure room 216. In another embodiment, the detectors 210 may be placed in the interior of the procedure room 216. If the detectors 210 sense an active RF wristband 204 near the entrance of or inside the procedure room 216, the detectors send a signal to the control 212 containing information that an active RF wristband 204 is sensed.

In one embodiment, the detectors 210 are operated to sense signals associated with the enabled or first mode of the active RF wristband 204 near or in the procedure room 216 by receiving signals transmitted from the active RF wristband 204. In another embodiment, the detectors 210 sense the presence of the enabled or first mode of the active RF wristband 204 by broadcasting an interrogating signal to active RF wristband 204. For example, the active RF wristband 204 may respond to the interrogating signal by transmitting a signal to the detectors 210 representing the enabled mode, e.g., the active or first mode, which indicates that the procedure site 208 has not been marked. Alternatively, the signal may represent the disabled mode, e.g., the inactive or second mode, which indicates that site 208 has been marked. On the other hand, the active RF wristband 204 may not respond to the interrogating signal from the detectors 210 and/or the detectors 210 may not receive a signal representing the enabled mode from the active RF wristband 204.

In yet another embodiment, the device would transmit one signal in the first mode and two signals in the second mode, one from the device and an added signal from an additional RF tag. In this case, the detectors 210 sense multiple signals from the device which is coupled with additional RF tags. For example, a wristband with an embedded RF or acousto-magnetic tag transmitting a first signal is applied to the patient 206. After the authorized individual marks the procedure site 208 on the body of the patient 206, the authorized individual applies to the wristband a modifying device, such as an additional RF or acousto-magnetic tag, indicating the procedure site 208 has been marked. The additional tag transmits a second signal different from the first signal of the first mode. As a result, the detectors 210 sense both the first signal from the embedded tag and the second signal from the additional tag indicating that the authorized individual has marked the procedure site 208 on the body of the patient 206. In other words, if the detectors 210 sense both the first signal from the embedded tag and the second signal from the additional tag, the detectors 210 would not send a signal to the control 212 and thus the alarm 214 would be silent. On the other hand, if the detectors 210 sense only the first signal from the embedded tag, which indicates that the second signal from the additional tag is absent and the procedure site 208 has not been marked, the detectors 210 would send a signal to the control 212 to energize the alarm 214. Also, if the detectors 210 do not sense either signal, the alarm 214 would not energized.

When the first signal from the embedded tag is detected, the detectors 210 transmit to the control 212 a signal containing information indicative of the first signal from the embedded tag. If the control 212 determines that the transmitted signal from the detectors 210 contains information indicating that the first signal from the embedded tag has been detected, the control 212 transmits a signal to the alarm 214, and the alarm 214 is energized to provide an indication that the first signal from the embedded tag is present and thus the procedure site 208 has not been marked. In other words, if the first signal is detected at 118, the detectors 210 activate the alarm, at 120, to alert health care personnel and/or the authorized individual that the patient has not been handled in compliance with the set of pre-procedure rules and a pre-procedure practice needs to be completed and/or the authorized individual has not deactivated the embedded tag after complying with the rules. In other words, the alarm 214 is responsive to the detectors 210 for providing an indication that only a first signal from the embedded tag has been detected, which indicates that one or more of the pre-procedure practices followed by a mode change have not been done. For example, site marking and deactivation may not have occurred so that 114 and 116 were bypassed as indicated by dashed line 126 connecting 112 and 118 in FIG. 1. As another example, site marking may have been done but deactivation may not have occurred so that 116 is bypassed as indicated by dashed line 128 connecting 114 and 118 in FIG. 1.

In an unlikely event that the detectors 210 sense only the signal of the second mode, the system 200 may be configured to notify the authorized individual, a nurse, an administrator or other health care personnel of such event. In other words, when the detectors 210 sense only the signal of the second mode (and not the signal of the first mode), this indicates that a procedure site has been marked or other pre-procedure rules have been complied with and that the patient is ready to undergo a procedure. However, failure to sense the signal of the first mode while sensing the signal of the second mode may indicate that the patient has not been fitted with the wristband with the embedded tag, or the embedded tag may be malfunctioned, or a combination thereof. Therefore, without departing from the spirit and the scope of the invention, the authorized individual or other responsible personnel would be notified of such occurrence.

Alternatively, it is also contemplated that the signal of a second mode may interfere with a signal of the first mode. In other words, the emitting signal of the second mode may be in the same frequency range as the signal of the first mode and may modify the signal of the first mode. For example, the second mode may be represented by a RF tag added to a RF bracelet, which bracelet represents the first mode. The signal transmitted by the tag would interfere with the signal transmitted by the bracelet to modify a parameter of the signal transmitted by the bracelet. The detectors 210 would detect the unmodified signal transmitted by the bracelet and initiate an alarm when such signal is detected. The detectors 210 would not initiate an alarm if signals, such as the modified signal of the bracelet or the signal of the RF tag, are transmitted.

In one embodiment, the alarm 214 may be a visual or an audible alarm. In another embodiment, if the alarm 214 is triggered, the authorized individual is required to complete the marking of the procedure site 208 and/or modification of the modes of the active RF wristband 204 before the performance of the procedure, according to the pre-procedure rules.

If an enabled active RF wristband 204 is not sensed, the procedure may be provided to the patient 206 at 122. When the authorized individual completes the procedure, the patient 206 is discharged at 124, pursuant to the facility's rules for discharging patients or other appropriate measures. In another embodiment where the patient may be subjected to multiple procedures that may not take place at one time, the patient 206 would be provided with another enabled device 204 at 110. This process may be required by the pre-procedure rules to ensure that an authorized individual personally marks another procedure site 208 and disables another active RF wristband 204 before the same patient subjects to anther procedure.

Alternatively, the device 204 may be activated or enabled after site marking in which case the detector would provide an alarm when a patient not having an enabled device enters the procedure room. In this case, the detector may have an infrared sensor or other sensor for sensing that a patient is entering the procedure room. If a patient is sensed and no enabled device is sensed, an alarm is provided.

It is also contemplated that, in a facility where one or more procedure room or other location is available for the authorized individual to perform procedures, the system illustrated in FIG. 2 may be used as an example in each of the procedure room or other location to monitor the status of the patient as described herein.

In operation, a health care facility, such as ambulatory surgery centers or doctor's offices, may use or practice various embodiments of the invention as follows. The facility has a set of pre-procedure rules, such as requiring a patient scheduled for a procedure is fitted with a wristband and/or an authorized individual to mark a particular site on the body of each patient before deactivating a wristband and before performing the procedure. The facility admits one or more patients and it is determined next whether each particular patient will receive a procedure. For each patient requiring a procedure, an active wristband is applied to or near the patients' body. On the other hand, if it is determined that a procedure is not necessary, the patients are treated according to a set of non-procedure rules established by the facility.

Once one of the identifying devices in the first mode is applied to each of the patients, according to the pre-procedure rules, only an authorized individual can mark a particular site on the body of each of patients before modifying the modes of each of the identifying devices. The authorized individual may use a marking instrument to mark the particular site on the body of each the patients. Thereafter, the authorized individual modifies the modes of each of the identifying devices from the first mode to the second mode. One or more detectors are placed in or near one or more procedure rooms where the procedure is to take place. If the detectors sense the first mode of one of the identifying devices near or in one of the procedure rooms, the detectors transmit a signal to the control 212 containing information that the first mode has been detected. The control sends a signal to one or more alarms if it determines that the first mode of one of the identifying devices has been detected. Each alarm provides an indication that the first mode is detected, indicating that the authorized individual has failed to mark the particular site on the body of each of the patients and/or to modify the mode of one of the identifying devices. Pursuant to the set of pre-procedure rules, the authorized individual must mark the particular site and/or modify the mode of one of the identifying devices before performing the procedure on the particular site on the body of each of the patients.

Figure 3:
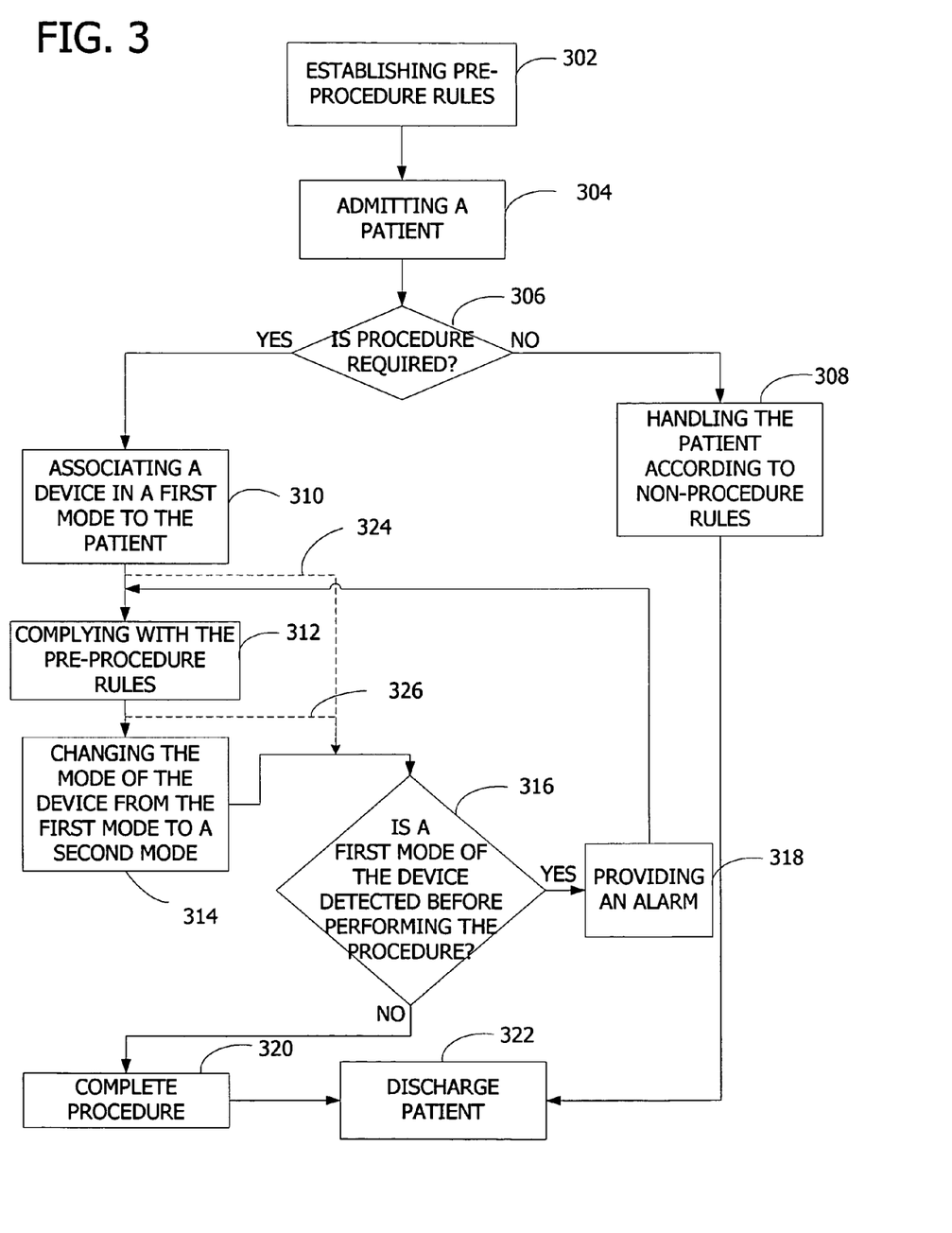
FIG. 3 is a flow chart of an embodiment of a method according to the invention for assisting in complying with pre-procedure rules.

Referring now to FIG. 3, a flow chart illustrates an embodiment for assisting in compliance with pre-procedure rules according to the invention. At 302, a facility establishes a set of pre-procedure rules, by its own management or by following recommendations from another organization, to assist in preparing a patient before a procedure. In one embodiment, such set of pre-procedure rules includes, but not is not limited to, requiring a course of action, such as associating a device to a patient scheduled for a procedure, marking a particular site on the body of a patient body prior to a procedure, measuring vital signs of a patient prior to a procedure and obtaining a consent from a patient prior to a procedure. As an example and not by way of limitation, the embodiment of FIG. 3 will be described with reference to a course of action which is required before a procedure.

At 304, the facility admits a patient according to its rules for admitting patients. A preliminary diagnosis or examination may take place before a health care professional, such as a doctor, determines whether a procedure is required for the patient at 306. If a procedure is required, a device in a first mode at 310 is associated with the patient. The device also has a second mode, the first mode and the second mode being distinctive. By associating the device with the patient, the device indicates the status of the patient as s/he is been handled prior to the procedure. Alternatively, if the procedure is not required, the facility may handle the patient according to its non-procedure rules and/or other appropriate measures at 308 would then be discharged at 322, according to the facility's rules for discharging patients or other appropriate measures.

Once the patient is associated with the device in the first mode, the patient is handled pursuant other courses of action to comply with the set of pre-procedure rules. At 312, the authorized individual complies with the pre-procedure rules by administering the course of action prior to the procedure. Thereafter, the mode of the device is changed from the first mode to the second mode by the authorized individual at 314. In one embodiment where measuring vital signs of the patient is one of the pre-procedure courses of action, changing of the mode is implemented by an authorized individual after measuring the patient's vital signs. In another embodiment where marking a particular site on the patient's body by the authorized individual is one of the pre-procedure courses of action, changing of the mode is implemented by an authorized individual after marking the particular site on the patient's body. In yet another embodiment where obtaining a consent from the patient is one of the pre-procedure courses of action, changing of the mode is implemented by an authorized individual after the patient's consent is obtained. In each case, this change in mode is accomplished before the procedure is performed. Compliance with the pre-procedure courses of action at 312 usually but not necessarily requires a compliance with all pre-procedure courses of action before changing the first mode to the second mode of the device indicating that the patient is ready for the scheduled procedure.

After changing the mode of the device from the first mode to the second mode, the patient associated with the device is taken to a procedure room where the procedure may be performed. A detector located near the entrance of or inside the procedure room senses for the first mode of the device near or inside the procedure room. If a device in the first mode is detected at 316, the detector activates an alarm, at 318, to alert health care personnel and/or the authorized individual that the patient has not been handled in compliance with the set of pre-procedure rules and a course of action needs to be completed and/or the authorized individual has not changed the mode of the device after completing the course of action. In other words, the alarm is responsive to the detector for providing an indication that a device has a mode which indicates that one or more of the pre-procedure courses of action followed by a mode change have not been complied with. For example, the course of action and mode change may not have occurred so that 312 and 314 were bypassed as indicated by dashed line 324 connecting 310 and 316 in FIG. 3. As another example, the course of action may have been done but mode change may not have occurred so that 314 is bypassed as indicated by dashed line 326 connecting 312 and 316 in FIG. 3.

As noted above, the detectors are sensing for devices in the first mode, which mode indicates that the pre-procedure practice has not been completed. It is also contemplated that the detector may be configured to detect devices in the second mode, which mode indicates that the pre-procedure practices have been completed. In this latter case, the alarm is activated when a patient without a device in the second mode is detected.

Alternatively, if a detected device is not in the first mode, the detector does not activate an alarm. This indicates that the set of pre-procedure courses of action has been complied with and the authorized individual has changed the mode of the device from the first mode to the second mode. The authorized individual may proceed to perform the procedure at 320 in the procedure room. Following the procedure, the patient is discharged at 322 pursuant to the facility's rules for discharging patients or other appropriate measures.

The order of execution or performance of the methods illustrated and described herein is not essential, unless otherwise specified. That is, elements of the methods may be performed in any order, unless otherwise specified, and that the methods may include more or less elements than those disclosed herein. For example, it is contemplated that executing or performing a particular element before, contemporaneously with, or after another element is within the scope of the invention.

When introducing elements of the present invention or the embodiment(s) thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that the several objects of the invention are achieved and other advantageous results attained.

As various changes could be made in the above system and method without departing from the scope of the invention, it is intended that all matter contained in the above description and shown in the accompanying drawings shall be interpreted as illustrative and not in a limiting sense.

What is claimed is:

1. A system for use with a patient scheduled to have a particular procedure at a particular site on the patient's body, said procedure to be performed in a procedure room, said system for monitoring the patient's status to determine whether the particular site has been marked before the procedure is performed, said system comprising:
    a device having a first mode indicating that the particular site of the patient has not been marked and adapted to be applied to the patient's body prior to the procedure;
    a modifying device for modifying the first mode to a second mode of the device wherein the second mode indicates that the particular site of the patient has been marked, the second mode being different from the first mode, said modifying device adapted for use after the particular site has been marked on the patient's body;
    a detector located at the procedure room to detect that the device having the first mode is located within an area near or in the procedure room; and
    an alarm responsive to the detector for providing an indication that a device having the first mode and not having the second mode has been detected within the area near or in the procedure room.

2. The system of claim 1, wherein the procedure will be performed in a procedure room and wherein the detector is located in a proximity of at least one of the following locations:
    the entrance of the procedure room before the patient enters the procedure room;
    the entrance of the procedure room as the patient enters the procedure room; and
    the interior of the procedure room.

3. The system of claim 2, wherein the procedure room is part of a facility, said facility being a hospital and/or clinic, and wherein a rule requiring marking of the particular site prior to the procedure is implemented.

4. The system of claim 1, wherein the device is an RF tag.

5. The system of claim 4, wherein the detector is an RF detector.

6. The system of claim 4, wherein the detector is an acousto-magnetic detector.

7. The system of claim 1, wherein the modifying device is an RF deactivator.

8. The system of claim 1, wherein the modifying device provides a visual or an audio indication of modification of modes.

9. The system of claim 1, wherein the device transmits a first signal in the first mode and wherein the device and/or any additions thereto transmit a second signal in the second mode, different from the signal of the first mode.

10. The system of claim 1, wherein the modifying device is an RF shield tag.

11. The system of claim 1, wherein the device is an acousto-magnetic tag.

12. The system of claim 1, wherein the modifying device is an acousto-magnetic deactivator.

13. The system of claim 1, wherein the modifying device is an acousto-magnetic shield tag.

14. A system for use with a plurality of patients, each particular patient scheduled to have a particular procedure at a particular site on the body of the particular patient, said procedures to be performed in a plurality of procedure rooms, said system for assisting in preventing the particular procedure of each patient being performed at a site on each patient's body other than the particular site, said system comprising:
    a plurality of devices, each device having a first mode and a second mode, each said device in the first mode adapted to be applied to the body of one of the patients prior to the particular procedure for each patient;
    a modifying device for changing each of the devices from the first mode to the second mode, said modifying device adapted for use after the particular site has been marked on each patient's body;
    a plurality of detectors, each detector located near or in one of the plurality of procedure rooms to detect the first mode of each of the plurality of devices; and
    a plurality of alarms, each alarm associated with one of the plurality of detectors for providing an indication when its associated detector detects one of the devices having the first mode.

15. The system of claim 14, wherein the procedures will be performed in a plurality of procedure rooms and wherein the detectors are located in a proximity of at least one of the following locations:
    the entrance of the procedure room before the patient enters the procedure room;
    the entrance of the procedure room as the patient enters the procedure room; and
    the interior of the procedure room.

16. The system of claim 14, wherein the procedure room is within a facility, said facility being a hospital and/or clinic, and wherein a rule requiring marking of each of the particular sites prior to the procedures is implemented.

17. The system of claim 14, wherein each device is an RF tag.

18. The system of claim 17, wherein each detector is an RF detector.

19. The system of claim 17, wherein each detector is an acousto-magnetic detector.

20. The system of claim 14, wherein each modifying device is an RF deactivator.

21. The system of claim 14, wherein each modifying device provides a visual or an audio indication of modification of modes.

22. The system of claim 14, wherein the device transmits a first signal in the first mode and wherein the device and/or any additions thereto transmit a second signal in the second mode, different from the first signal of the first mode.

23. The system of claim 14, wherein each modifying device is an RF shield tag.

24. The system of claim 14, wherein each device is an acousto-magnetic tag.

25. The system of claim 14, wherein each modifying device is an acousto-magnetic deactivator.

26. The system of claim 14, wherein each modifying device is an acousto-magnetic shield tag.

27. A system for use with a patient scheduled to have a procedure at a facility with pre-procedure rules, said system for monitoring the patient's status to determine whether the patient has been handled in compliance with the pre-procedure rules prior to performing the procedure on the patient, said system comprising:

a device having a mode and adapted to be applied to the patient's body prior to the procedure;

a modifying device for modifying the mode to another mode of the device, said modifying device adapted for use after a compliance with the pre-procedure rules;

a detector to detect the mode of the device; and an alarm responsive to the detector for providing an indication that a device has a mode which indicates that the pre-procedure rules have not been complied with.

28. The system of claim 27, wherein the procedure is will be performed in a procedure room at the facility and the detector is located in a proximity of at least one of the following locations:

the entrance of the procedure room in the facility before the patient enters the procedure room;

the entrance of the procedure room in the facility as the patient enters the procedure room; and the interior of the procedure room in the facility.

29. The system of claim 28, wherein the procedure room is part of the facility, said facility being a hospital and/or clinic, and wherein at least one of the following pre-procedure rules is implemented:

marking the particular site on the patient's body prior to the procedure;

measuring vital signs of the patient prior to the procedure; and obtaining a consent from the patient prior to the procedure.

30. The system of claim 29, wherein the rules require that only an authorized individual is permitted to perform the pre-procedure and/or change the mode.

31. The system of claim 27, wherein the compliance with the pre-procedure rules includes measuring vital signs of the patient prior to the procedure, wherein the modifying device modifies the mode to the another mode of the device after measuring the vital signs of the patient.

32. The system of claim 27, wherein the compliance with the pre-procedure rules includes obtaining a consent from the patient prior to the procedure, wherein the modifying device modifies the mode to the another mode of the device after obtaining the consent from the patient.

33. The system of claim 27, wherein the device is an RF tag.

34. The system of claim 33, wherein the detector is an RF detector.

35. The system of claim 33, wherein the detector is an acousto-magnetic detector.

36. The system of claim 27, wherein the modifying device is an RF deactivator.

37. The system of claim 27, wherein the modifying device provides a visual or an audio indication of modification of modes.

38. The system of claim 27, wherein the device transmits a first signal in the mode and wherein the device and/or any additions thereto transmit a second signal in the another mode, different from the first signal of the mode.

39. The system of claim 27, wherein the modifying device is an RF shield tag.

40. The system of claim 27, wherein the device is an acousto-magnetic tag.

41. The system of claim 27, wherein the modifying device is an acousto-magnetic deactivator.

42. The system of claim 27, wherein the modifying device is an acousto-magnetic shield tag.

43. The system of claim 27, wherein the compliance with the pre-procedure rules includes marking a particular site on the patient's body prior to the procedure, wherein the modifying device modifies the mode to the another mode of the device after marking the particular site on the patient's body.

* * * * *